(12) United States Patent
Ferrera (10) Patent No.: US 6,168,570 B1
(45) Date of Patent: Jan. 2, 2001

(54) MICRO-STRAND CABLE WITH ENHANCED RADIOPACITY

(75) Inventor: David A. Ferrera, San Francisco, CA (US)

(73) Assignee: Micrus Corporation, Mountain View, CA (US)

( * ) Notice: Under 35 U.S.C. 154(b), the term of this patent shall be extended for 0 days.

This patent is subject to a terminal disclaimer.

(21) Appl. No.: 09/245,430

(22) Filed: Feb. 5, 1999

Related U.S. Application Data (63) Continuation of application No. 08/986,004, filed on Dec. 5, 1997.

(51) Int. Cl.$^7$ .............................. A61B 5/00; A61M 25/00
(52) U.S. Cl. .......................... 600/585; 606/108; 606/194
(58) Field of Search .................................. 600/434, 435, 600/585; 606/108, 194, 191, 200; 604/52, 57; 140/149

(56) References Cited

U.S. PATENT DOCUMENTS

| | | |
|---|---|---|
| 1,341,052 | 5/1920 | Gale . |
| 1,667,730 | 5/1928 | Green . |
| 2,078,182 | 4/1937 | MacFarland . |
| 2,549,335 | 4/1951 | Rahthus . |
| 3,334,629 | 8/1967 | Cohn . |
| 3,485,234 | 12/1969 | Stevens . |
| 3,612,058 * | 10/1971 | Ackerman ............................... 128/348 |
| 3,649,224 | 3/1972 | Anderson et al. . |
| 3,868,956 | 3/1975 | Alfidi et al. . |
| 4,161,952 | 7/1979 | Kinney et al. . |
| 4,257,421 | 3/1981 | Beal ........................................ 128/348 |
| 4,494,531 | 1/1985 | Gianturco . |
| 4,512,338 | 4/1985 | Balko et al. . |

(List continued on next page.)

FOREIGN PATENT DOCUMENTS

| | | |
|---|---|---|
| 32 03 410 A1 | 2/1982 | (DE) . |
| 4102550 A1 | 8/1991 | (DE) . |
| A 61 F 2/04 | 2/1997 | (DE) . |

(List continued on next page.)

OTHER PUBLICATIONS

"Neurosurgery Interactive Article Part 2 –Clinical Studies Embolization of Cerebral Arteriovenous Malformations: Part II–Aspects of Complications and Late Outcome" By Christopher Lundqvist, M.D., Ph. D, G. Wilkolm, M.D., Ph.D., P. Svendsen, M.D., Ph.D., Sep. 1996, pp. 1–16.

(List continued on next page.)

Primary Examiner—Cary O'Connor
Assistant Examiner—Charles Marmor, II
(74) Attorney, Agent, or Firm—Fulwider Patton Lee & Utecht, LLP; James W. Paul (57) ABSTRACT

This invention relates generally to emplacable devices for interventional therapeutic treatment or vascular surgery, and more particularly concerns a stranded micro-cable with enhanced radiopacity that can be used to fabricate a vascular device, a stent, a guidewire or the like. The micro-cable is made of strands of a material exhibiting super-elasticity or shape memory properties, such as nickel-titanium, and includes a strand of radiopaque material, such as platinum or gold, in order to provide a radiopaque marker during interventional therapeutic treatment or vascular surgery. The micro-cable can be used to form occluding coils which can be used in devices to restrict, reinforce, or to occlude areas of small diameter vasculature such as an aneurysm or malformation in an artery or vein in the brain.

20 Claims, 8 Drawing Sheets

U.S. PATENT DOCUMENTS

| | | | |
|---|---|---|---|
| 4,548,206 | 10/1985 | Osborne | 128/772 |
| 4,553,545 | 11/1985 | Maass et al. . | |
| 4,579,127 * | 4/1986 | Haacke | 128/772 |
| 4,611,390 * | 9/1986 | Tanaka et al. | 29/599 |
| 4,629,458 | 12/1986 | Pinchuk . | |
| 4,638,803 | 1/1987 | Rand . | |
| 4,655,771 | 4/1987 | Wallsten . | |
| 4,670,286 | 6/1987 | Nyilas et al. . | |
| 4,682,607 | 7/1987 | Vaillancourt et al. . | |
| 4,718,907 | 1/1988 | Karwoski et al. . | |
| 4,732,152 | 3/1988 | Wallstén et al. . | |
| 4,748,986 | 6/1988 | Morrison et al. . | |
| 4,768,507 | 9/1988 | Fischell et al. . | |
| 4,795,458 | 1/1989 | Regan . | |
| 4,798,606 | 1/1989 | Pinchuk . | |
| 4,800,882 | 1/1989 | Gianturco . | |
| 4,813,925 | 3/1989 | Anderson, Jr. et al. . | |
| 4,820,298 | 4/1989 | Leveen et al. . | |
| 4,830,003 | 5/1989 | Wolff et al. . | |
| 4,850,960 | 7/1989 | Grayzel . | |
| 4,856,516 | 8/1989 | Hillstead . | |
| 4,873,978 | 10/1989 | Ginsburg . | |
| 4,922,924 | 5/1990 | Gambale et al. . | |
| 4,932,419 | 6/1990 | de Toledo . | |
| 4,945,342 * | 7/1990 | Steinemann | 174/113 R |
| 4,950,258 | 8/1990 | Kawai et al. . | |
| 4,954,126 | 9/1990 | Wallstén . | |
| 4,957,479 | 9/1990 | Roemer . | |
| 4,957,501 | 9/1990 | Lahille et al. . | |
| 4,990,155 | 2/1991 | Wilkoff . | |
| 4,994,069 | 2/1991 | Ritchart et al. . | |
| 4,998,916 | 3/1991 | Hammerslag et al. . | |
| 5,015,253 | 5/1991 | MacGregor . | |
| 5,019,090 | 5/1991 | Pinchuk . | |
| 5,025,799 | 6/1991 | Wilson . | |
| 5,026,377 | 6/1991 | Burton et al. . | |
| 5,035,706 | 7/1991 | Giantureo et al. . | |
| 5,037,377 | 8/1991 | Alonso . | |
| 5,037,391 | 8/1991 | Hammerslag et al. . | |
| 5,041,084 | 8/1991 | DeVries et al. . | |
| 5,041,126 | 8/1991 | Gianturco . | |
| 5,055,101 | 10/1991 | McCoy . | |
| 5,061,275 | 10/1991 | Wallstén et al. . | |
| 5,063,935 | 11/1991 | Gambale . | |
| 5,064,435 | 11/1991 | Porter . | |
| 5,071,407 | 12/1991 | Termin et al. . | |
| 5,092,847 | 3/1992 | Pozzo . | |
| 5,104,404 | 4/1992 | Wolff . | |
| 5,108,407 | 4/1992 | Geremia et al. . | |
| 5,122,136 | 6/1992 | Guglielmi et al. . | |
| 5,133,731 | 7/1992 | Butler et al. . | |
| 5,133,732 | 7/1992 | Wiktor . | |
| 5,139,243 | 8/1992 | Balsells | 267/167 |
| 5,141,502 | 8/1992 | Macaluso, Jr. . | |
| 5,147,370 | 9/1992 | McNamara et al. . | |
| 5,151,105 | 9/1992 | Kwan-Gett . | |
| 5,152,784 | 10/1992 | Tsilibary . | |
| 5,160,341 | 11/1992 | Brenneman et al. . | |
| 5,165,421 * | 11/1992 | Fleischhacker et al. | 128/772 |
| 5,167,233 | 12/1992 | Eberle et al. . | |
| 5,171,273 | 12/1992 | Silver et al. . | |
| 5,174,302 | 12/1992 | Palmer . | |
| 5,176,625 | 1/1993 | Brisson . | |
| 5,176,661 | 1/1993 | Evard et al. . | |
| 5,183,085 | 2/1993 | Timmermans . | |
| 5,186,992 | 2/1993 | Kite, III . | |
| 5,197,977 | 3/1993 | Hoffman, Jr. et al. . | |
| 5,203,772 | 4/1993 | Hammerslag et al. . | |
| 5,211,183 | 5/1993 | Wilson . | |
| 5,213,111 | 5/1993 | Cook et al. . | |
| 5,217,484 | 6/1993 | Marks . | |
| 5,221,270 | 6/1993 | Parker | 604/282 |
| 5,222,969 | 6/1993 | Gillis . | |
| 5,226,911 | 7/1993 | Chee et al. . | |
| 5,228,453 | 7/1993 | Sepetka . | |
| 5,230,348 | 7/1993 | Ishibe et al. . | |
| 5,234,437 | 8/1993 | Sepetka | 606/108 |
| 5,234,456 | 8/1993 | Silvestrini . | |
| 5,238,004 | 8/1993 | Sahatjian et al. . | |
| 5,243,996 | 9/1993 | Hall . | |
| 5,246,014 | 9/1993 | Williams et al. . | |
| 5,250,071 | 10/1993 | Palermo . | |
| 5,251,640 | 10/1993 | Osborne . | |
| 5,256,146 | 10/1993 | Ensminger et al. . | |
| 5,259,393 | 11/1993 | Corso, Jr. et al. . | |
| 5,261,916 | 11/1993 | Engelson | 606/108 |
| 5,304,194 | 4/1994 | Chee et al. . | |
| 5,304,195 | 4/1994 | Twyford, Jr. et al. | 606/191 |
| 5,312,356 | 5/1994 | Endelson et al. | 604/164 |
| 5,312,415 | 5/1994 | Palermo . | |
| 5,334,210 | 8/1994 | Gianturco | 606/151 |
| 5,336,205 | 8/1994 | Zenzen et al. . | |
| 5,341,818 | 8/1994 | Abrams et al. . | |
| 5,342,387 | 8/1994 | Summers . | |
| 5,344,315 * | 9/1994 | Hanson | 433/20 |
| 5,350,397 | 9/1994 | Palermo et al. . | |
| 5,354,295 | 10/1994 | Guglielmi et al. . | |
| 5,368,049 | 11/1994 | Raman et al. . | |
| 5,373,856 | 12/1994 | Grenouillet . | |
| 5,375,404 * | 12/1994 | Conway | 57/212 |
| 5,380,304 | 1/1995 | Parker | 604/282 |
| 5,382,259 | 1/1995 | Phelps et al. . | |
| 5,383,887 | 1/1995 | Nadal . | |
| 5,386,828 | 2/1995 | Owens et al. . | |
| 5,395,390 | 3/1995 | Simon et al. . | |
| 5,406,377 | 4/1995 | Cragg . | |
| 5,409,015 | 4/1995 | Palermo . | |
| 5,413,597 | 5/1995 | Krajicek . | |
| 5,415,664 | 5/1995 | Pinchuk . | |
| 5,423,829 | 6/1995 | Pham et al. | 600/108 |
| 5,423,849 | 6/1995 | Engelson et al. . | |
| 5,433,723 | 7/1995 | Lindenberg et al. . | |
| 5,439,485 | 8/1995 | Mar et al. . | |
| 5,441,516 | 8/1995 | Wang et al. . | |
| 5,443,478 | 8/1995 | Purdy . | |
| 5,483,022 * | 1/1996 | Mar | 174/128.1 |
| 5,484,449 | 1/1996 | Amundson et al. . | |
| 5,500,013 | 3/1996 | Buscemi et al. . | |
| 5,509,411 | 4/1996 | Littmann et al. . | |
| 5,514,115 | 5/1996 | Frantzen et al. . | |
| 5,514,128 | 5/1996 | Hillsman et al. . | |
| 5,514,176 | 5/1996 | Bosley, Jr. . | |
| 5,519,172 | 5/1996 | Spencer et al. . | |
| 5,520,194 | 5/1996 | Miyata et al. . | |
| 5,522,836 | 6/1996 | Palermo . | |
| 5,523,092 | 6/1996 | Hanson et al. . | |
| 5,536,274 | 7/1996 | Neuss | 623/108 |
| 5,540,701 | 7/1996 | Sharkey et al. . | |
| 5,540,713 | 7/1996 | Schnepp-Pesch et al. . | |
| 5,549,624 | 8/1996 | Mirigian et al. . | |
| 5,549,663 | 8/1996 | Cottone, Jr. . | |
| 5,562,641 | 10/1996 | Flomenblit et al. . | |
| 5,569,245 | 10/1996 | Guglielmi et al. . | |
| 5,582,619 | 12/1996 | Ken . | |
| 5,601,593 | 2/1997 | Freitag . | |
| 5,603,694 | 2/1997 | Brown et al. . | |
| 5,607,445 | 3/1997 | Summers . | |
| 5,609,627 | 3/1997 | Goicoechea et al. . | |
| 5,613,981 | 3/1997 | Boyle et al. . | |
| 5,618,301 | 4/1997 | Hauenstein et al. . | |
| 5,624,461 | 4/1997 | Mariant . | |

| | | |
|---|---|---|
| 5,632,772 | 5/1997 | Alcime et al. . |
| 5,637,113 | 6/1997 | Tartaglia et al. . |
| 5,639,277 | 6/1997 | Mariant et al. . |
| 5,643,254 | 7/1997 | Scheldrup et al. . |
| 5,645,082 | 7/1997 | Sung et al. ............................... 128/897 |
| 5,645,558 | 7/1997 | Horton .................................... 606/191 |
| 5,649,949 | 7/1997 | Wallace et al. . |
| 5,667,522 | 9/1997 | Flomenblit et al. . |
| 5,669,931 | 9/1997 | Kupiecki et al. ........................ 606/191 |
| 5,676,697 | 10/1997 | McDonald . |
| 5,685,322 | 11/1997 | Sung et al. ............................... 128/897 |
| 5,690,643 | 11/1997 | Wijay . |
| 5,690,666 | 11/1997 | Berenstein et al. . |
| 5,690,667 | 11/1997 | Gia .......................................... 606/191 |
| 5,690,671 | 11/1997 | McGurk et al. . |
| 5,693,067 | 12/1997 | Purdy ..................................... 606/200 |
| 5,693,085 | 12/1997 | Buirge et al. . |
| 5,700,258 | 12/1997 | Mirigian et al. ............................ 606/1 |
| 5,702,373 | 12/1997 | Samson . |
| 5,707,389 | 1/1998 | Louw et al. ............................. 606/200 |
| 5,718,711 | 2/1998 | Berenstein et al. ..................... 606/191 |
| 5,725,534 | 3/1998 | Rasmussen .............................. 606/108 |
| 5,725,572 | 3/1998 | Lam et al. .................................. 623/1 |
| 5,733,326 | 3/1998 | Tomonto et al. ........................... 623/1 |
| 5,733,329 | 3/1998 | Wallace et al. ............................. 623/1 |
| 5,741,327 | 4/1998 | Frantzen ..................................... 623/1 |
| 5,743,905 | 4/1998 | Eder et al. ................................. 606/32 |
| 5,746,769 | 5/1998 | Ton et al. ................................. 606/206 |
| 5,749,891 | 5/1998 | Ken et al. ................................ 606/200 |
| 5,749,894 | 5/1998 | Engelson ................................. 606/213 |
| 5,762,615 | 6/1998 | Weier ...................................... 600/585 |
| 5,766,160 | 6/1998 | Samson et al. ............................. 606/1 |
| 5,800,453 | 9/1998 | Gia .......................................... 606/191 |
| 5,800,455 | 9/1998 | Palermo et al. ......................... 606/191 |
| 5,800,511 | 9/1998 | Mayer ........................................ 623/1 |
| 5,814,062 | 9/1998 | Sepetka et al. .......................... 606/198 |
| 5,817,100 | 10/1998 | Igaki ....................................... 606/108 |
| 5,843,118 | 12/1998 | Sepetka et al. .......................... 606/194 |
| 5,897,584 * | 4/1999 | Herman ................................... 607/122 |
| 6,045,497 * | 4/2000 | Schweich, Jr. et al. .................. 600/16 |

FOREIGN PATENT DOCUMENTS

| | | |
|---|---|---|
| 0 183 372 A1 | 6/1986 | (EP) . |
| 0 278 937 | 8/1988 | (EP) . |
| 0 382014 A1 | 8/1990 | (EP) . |
| 0 518 704 A1 | 12/1992 | (EP) . |
| 0 627 201 A1 | 12/1994 | (EP) . |
| 0 743 047 A2 | 11/1996 | (EP) . |
| 0 747 014 A1 | 11/1996 | (EP) . |
| 0 743 047 A3 | 3/1997 | (EP) . |
| 0 820 726 A2 | 1/1998 | (EP) . |
| 592 182 | 7/1925 | (FR) . |
| 2 066 839 | 7/1981 | (GB) . |
| WO 94/14408 | 9/1992 | (WO) . |
| WO 94/09705 | 5/1994 | (WO) . |
| WO 94/10936 | 5/1994 | (WO) . |
| WO 94/16629 | 8/1994 | (WO) . |
| WO 94/18585 | 7/1995 | (WO) . |
| WO 95/21592 | 8/1995 | (WO) . |
| WO 97/26939 | 7/1997 | (WO) . |
| WO 97/48351 | 12/1997 | (WO) . |
| WO 99/07294 | 2/1999 | (WO) . |
| WO 99/29260 | 6/1999 | (WO) . |

OTHER PUBLICATIONS

"Shape Memory Alloys" By Jeff Perkins, pp. 1095–1096.

"Treatment of Large and Giant Fusiform Intracranial Aneurysms with Guglielmi Detachable Coils", By Y. Pierre Gobin, M.D., et al., J. Neurosurg., Jan. 1996, pp. 55–62, vol. 84.

"Endovascular Treatment of Basilar Tip Aneurysms Using Electrolytically Detachable Coils", By Cameron G. McDougall, M.D., et al., J. Neurosurg., Mar. 1996, pp. 393–399, vol. 84.

"Retrieval of Giglielmi Detachable Coil After Unraveling and Fracture: Case Report and Experimental Results", By Scott C. Standard, M.D., et al., Neurosurgery, Nov. 1994, pp. 994–999, vol. 35, No. 5.

"Catheters, Embolic Agents Spark Neurointervention", By Gary Duckwiller, M.D., et al., Diagnostic Imaging, May 1994, pp. 66–70 & 102.

Copy of International Search Report Relating to PCT/US97/10882 Dated Nov. 6, 1997.

Copy of International Preliminary Examination Report Relating To PCT/US97/10882 Dated Aug. 10, 1998.

Christos A. Athanasoulis, M.D., The New England Journal of Medicine, May 15, 1980, "Therapeutic Applications of Angiography" pp. 1117–1125 (1 of 2).

Christos A. Athanasoulis, M.D., The New England Journal of Medicine, May 22, 1980, "Therapeutic Applications of Angiography" pp. 1174–1179 (2 of 2).

Alex Berenstein, M.D., and Irvin I. Kricheff, M.D., "Catheter and Material Selection for Transarterial Embolization: Technical Considerations" Radiology, Sep. 1979; pp. 631–639.

O.A. Battista, et al. Journal of Applied Polymer Science 1967 "Colloidal Macromolecular Phenomena. Part II. Novel Microcrystals of Polymers" pp. 481–498.

Sadek K. Hilal, M.D. et al. Journal of Neurological Surgery "Therapeutic Percutaneous Embolization for Extra–Axial Vascular Lesions of The Head, Neck and Spine" Sep. 1975; pp. 275–287.

Stephen L. Kaufman, M.D. et al. Investigative Radiology, May–Jun. 1978, "Transcatheter Embolization with Microfibrillar Collagen In Swine"; pp. 200–204.

Ashok J. Kumar, et al., Journal of Neuroradiology (1982) "Preoperative Embolization of Hypervascular Head and Neck Neoplasms Using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975, "Selective Arterial Embolization for Control of Massive Upper Gastrointestinal Bleeding" pp. 119–126.

Glenn H. Roberson, et al., American Journal of Radiology, Oct. 1979, "Therapeutic Embolization of Juvenile Angiofibroma" pp. 657–663.

Sidney Wallace, M.D. et al., Cancer, Oct. 1979, "Arterial Occlusion of Pelvic Bone Tumors"; pp. 322–325 & 661–663.

"Mechanical Devices for Arterial Occlusion" By C. Gianturco, M.D., et al., Jul. 1975, pp. 428–435.

"Therapeutic Vascular Occlusion Utilizing Steel Coil Technique: Clinical Applications" By Sidney Wallace, et al., Amj. Roentgenol (1976); pp. 381–387.

"Transcatheter Intravascular Coil Occlusion of Experimental Arteriovenous Fistulas", By James H. Anderson, et al., Am. J. Roentgenol, Nov. 1977, pp. 795–798.

"'Mini' Gianturco Stainless Steel Coils for Transcatheter Vascular Occlusion" By James H. Anderson, et al., From The Department of Diagnostic Radiology at The University of Texas System Cancer Center, Aug. 1978, pp. 301–303.

"A New Improved Coil for Tapered–Tip Catheter for Arterial Occlusion" by Vincent P. Chuang, M.D., et al., May 1980, pp. 507–509.

* cited by examiner

MICRO-STRAND CABLE WITH ENHANCED RADIOPACITY

RELATED APPLICATIONS

This is a continuation of Ser. No. 08/986,004 filed Dec. 5, 1997.

BACKGROUND OF THE INVENTION

1. Field of the Invention

This invention relates generally to implantable devices for interventional therapeutic treatment or vascular surgery, and more particularly concerns a stranded micro-cable with enhanced radiopacity that can be used to fabricate a vascular device, a stent, a guidewire or the like.

2. Description of Related Art

The art and science of interventional therapy and surgery has continually progressed towards treatment of internal defects and diseases by use of ever smaller incisions or access through the vasculature or body openings in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel or the like and the use of vasoocclusive devices to treat defects in the vasculature. There is a constant drive by those practicing in the art to develop new and more capable systems for such applications. When coupled with developments in biological treatment capabilities, there is an expanding need for technologies that enhance the performance of interventional therapeutic devices and systems.

One specific field of interventional therapy that has been able to advantageously use recent developments in technology is the treatment of neurovascular defects. More specifically, as smaller and more capable structures and materials have been developed, treatment of vascular defects in the human brain which were previously untreatable or represented unacceptable risks via conventional surgery have become amenable to treatment. One type of non-surgical therapy that has become advantageous for the treatment of defects in the neurovasculature has been the placement by way of a catheter of vasoocclusive devices in a damaged portion of a vein or artery.

Vasoocclusion devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a pre-formed strand of flexible material that can be a nickel-titanium alloy is known from U.S. Pat. No. 5,645,558, which is specifically incorporated by reference herein.

The delivery of such vasoocclusive devices can be accomplished by a variety of means, including via a catheter in which the device is pushed through the catheter by a pusher to deploy the device. The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

For treatment of areas of the small diameter vasculature such as a small artery or vein in the brain, for example, and for treatment of aneurysms and the like, micro-coils formed of very small diameter wire are used in order to restrict, reinforce, or to occlude such small diameter areas of the vasculature. A variety of materials have been suggested for use in such micro-coils, including nickel-titanium alloys, copper, stainless steel, platinum, tungsten, various plastics or the like, each of which offers certain benefits in various applications. Nickel-titanium alloys are particularly advantageous for the fabrication of such micro coils, in that they can have super-elastic or shape memory properties, and thus can be manufactured to easily fit into a linear portion of a catheter, but attain their originally formed, more complex shape when deployed. Although various materials are more or less kink resistant when nickel-titanium alloys are dimensioned into wire smaller than approximately 0.010 inches in diameter, they can have low yield strength and can kink more easily, thus severely limiting the applications for such finely drawn wire in the fabrication of vasoocclusive devices. As a further limitation to such applications, nickel-titanium alloys are also not radiopaque in small diameters, and a single nickel-titanium wire would need to be approximately 0.012 inches in diameter to be even slightly radiopaque. However, such a thickness of a single nickel-titanium wire would unfortunately also be relatively stiff and possibly traumatic to the placement site, particularly if used for treatment of delicate and already damaged areas of the small diameter vasculature such as an aneurysm in an artery or vein in the brain, for example.

One conventional guidewire for use in a catheter is known that is made of a high elasticity nickel-titanium alloy, and is useful for accessing peripheral or soft tissue targets. The distal tip of the guidewire is provided with a radiopaque flexible coil tip, and a radiopaque end cap is attached to the guidewire by a radiopaque ribbon. Such a construction is complex to manufacture, fragile and can potentially break off during use with undesirable results. A stretch resistant vasoocclusive coil is also known that can be made of a primary helically wound coil of platinum wire, with a stretch-resisting wire attached within the primary coil between two end caps. Unfortunately, such a construction is relatively difficult to fabricate and also fragile, allowing for the possibility of the fracture of the central radiopaque wire, the coil, the welds or some combination of them, and it can also potentially break off during use. Also, such a construction has a complex and nonlinear bending characteristic, dependent on the spacing of the coils and central wire and the radius of the bend of the coil.

From the above, it can be seen that vasoocclusive devices and their attendant deployment systems provide important improvements in the treatment of damaged neurovascular areas. However, there remain important limitations in the technology presently available to fabricate these devices. It would therefore be desirable to provide a structural element that can be incorporated into a stent, guidewire, micro-coil or the like, which offers the advantages of a shape memory alloy such as a nickel-titanium alloy, and that incorporates radiopaque material in a stable configuration that is not subject to breaking during use of the device, so that the device can be visualized under fluoroscopy. The present invention meets these and other needs.

SUMMARY OF THE INVENTION

Significant advances have been made in the treatment of neurovascular defects without resolution to surgery. More specifically, micro catheters have been developed which allow the placement of vasooclusive devices in an area of the vasculature which has been damaged. In presently used techniques, the vasooclusive devices take the form of spiral wound wires that can take more complex three dimensional shapes as they are inserted into the area to be treated. By using materials that are highly flexible, or even super-elastic and relatively small in diameter, the wires can be installed in a micro-catheter in a relatively linear configuration and assume a more complex shape as it is forced from the distal end of the catheter.

In order to gain the advantages presently being realized with micro-catheter therapies and procedures to repair damage to the vasculature in the brain and other vessels, shape memory materials such as nickel-titanium alloys have been incorporated in vasooclusive devices to be placed by the catheters. However, the range of diameters of wire and the configurations of the resulting geometry of both the coils and the devices developed which can be used have been limited by both the relatively small diameter of wire that must be used to avoid trauma and allow housing within the catheter prior to deployment, and the requirement for larger diameters to provide for radiopaque markers and mechanical robustness. In many cases this has resulted in primary wire characteristics in the coil that are unacceptably stiff, very delicate, or subject to kinking. The present invention obtains significant advantages over such prior art devices by providing a cable of multiple strands of an alloy adapted to be used in catheters, stents, vasooclusive devices, guidewires and the like, thus providing a kink resistant, high strength material with highly desirable performance characteristics which can be altered by construction details to suit a variety of interventional therapeutic procedures.

More specifically, it has been found that single strands of small diameter nickel-titanium alloys, as well as other metal alloys, used to form vasooclusive devices can be kinked if twisted and pulled as can occur during or after deployment from a catheter, especially if the doctor wishes to withdraw a partially deployed coil because it is somehow incorrect in size, shape or length to repair the damage to the vessel. Also, single wire coils are more likely to cause trauma to the area to be treated if the wire is of a sufficient diameter to provide adequate tensile strength. Furthermore, such small diameter wires of some of these materials such as nickel-titanium, stainless steel and the like, are not generally radiopaque with currently available equipment, necessitating the use of radiopaque markers attached to the device, with the resultant possible diminution of functionality and increased diameter.

The present invention solves these and other problems by providing, in its broadest aspect, a micro-cable which includes at least one radiopaque strand to offer a continuous indication under fluoroscopy of the deployed configuration of the device incorporating the micro-cable. When combined with the benefits of a material such as nickel-titanium in the other strands of the micro-cable, numerous advantages are available from the use of this basic construction in interventional medicine.

Briefly, and in general terms, a presently preferred embodiment of the present invention provides for a multi-stranded micro-cable made of a suitable material such as stainless steel or a nickel-titanium alloy, with the cable including at least one radiopaque strand, made of platinum, tungsten or gold, in order to serve as a marker during a procedure. The multi-stranded micro-cable can be configured into a stent, guidewire, micro-coil or the like used in micro-catheters, for example, to restrict, reinforce, or to occlude areas of the small diameter vasculature such as an artery or vein in the brain, for example, for treatment of aneurysms and the like.

In one presently preferred embodiment, the invention accordingly provides for a multi-stranded micro-cable formed of a plurality of flexible strands of a super elastic material, and at least one radiopaque strand. In one presently preferred embodiment, the multi-stranded micro-cable comprises a plurality of flexible strands of nickel-titanium alloy, the micro cable having at least one central axially disposed radiopaque wire, such as platinum, tungsten or gold, for example, in order to provide a radiopaque marker during vascular procedures. In this preferred embodiment, the construction of the invention places the lowest tensile strength and highest flexibility member, the radiopaque marker strand, in a position in the cable which results in minimum stress on that member; at the same time, the super elastic material is in the outer strands, which have the dominant affect on performance parameters, thus enhancing the benefits of the material. Another benefit associated with the invention compared to prior art devices is that the multiple stranded cable configuration, in addition to providing a highly flexible and resilient structure, eliminates the necessity of a safety wire, since the failure of a single strand will not cause a severing of the cable. Also, the construction prevents stretching of the cable in the event of failure of a single strand, which is a significant benefit compared to constructions which have a coil around a central safety wire.

In a second presently preferred embodiment, the invention includes a multi stranded cable constructed of multiple twisted strands of a suitable material such as a shape memory alloy or super elastic alloy of nickel-titanium, with one or more of the twisted strands consisting of a radiopaque material. The radiopaque strand may be one or more of the peripheral twisted strands and may also include one or more central strands of the cable. In a preferred aspect of the embodiment, the cable consists of six peripheral twisted strands and a central linear core strand, one or more of which can be of radiopaque material.

In a third aspect of the invention, the cable can be of linear strands that are arranged in a bundle and fastened or bound at intervals, or continuously, in order to maintain contact among the strands as the cable is bent. One or more of the strands may be radiopaque. This construction is adaptable to guidewires and other structures that must be pushable and/or torqueable, but still remain highly flexible and include radiopacity. Variations on this embodiment can include an outer sheath which consists of a solid or helically wound cover to provide enhanced torqueability and pushability. More specifically, the outer sheath can vary in thickness, stiffness of material or spring of the sheath members to provide desired variations in bending or stiffness of the cable. Such a construction is particularly adaptable to guidewires and the like, and can be varied in terms of the binding or outer layer to alter the torqueability of the cable, and the flexibility of the cable can be varied along its length by the number and sizes of the stranded members in the cable.

In a fourth aspect of the invention, one or more of the strands can be of a therapeutic material used to enhance treatment of the site after placement of the device. In one presently preferred embodiment of the invention, the cable includes twisted strands of wire around the periphery of the cable, at least one of which is radiopaque. The core of the cable contains a therapeutic agent such as human growth hormone, genetic material, antigens or the like that are intended to become active after placement. Such a construction can be adapted to a variety of interventional therapeutic treatments. In one aspect of this embodiment, one of the strands can have multiple functions, such as providing both a therapeutic effect and also contributing to the structural integrity of the cable. By using copper in such a micro-cable, for instance, the copper can enhance the use of a device made from the cable as on interuterine device, with the copper also contributing to the radiopacity and structural integrity of the micro-cable. In the event that such an effect is desired, the therapeutic strand can be placed on the exterior of the cable to enhance contact with the site to be treated.

These and other aspects and advantages of the invention will become apparent from the following detailed description and the accompanying drawing, which illustrates by way of example the features of the invention.

DETAILED DESCRIPTION OF THE PREFERRED EMBODIMENTS

While nickel-titanium alloys are useful in forming super-elastic or shape memory interventional devices, micro-coils formed of very small diameter wires of nickel-titanium alloy material for treatment of areas of the small diameter vasculature such as an artery or vein in the brain, for treatment of aneurysms and the like, for example, can have relatively low yield strengths and are somewhat subject to kinking, even if made of super-elastic alloy. This can create problems if the coil is to be withdrawn after being emplaced by the doctor, as for instance, if the device is too small to effectively fill the cavity to be treated. Furthermore, even solid wires of a size suitable for use in interventional devices are not very radiopaque.

As is illustrated in the drawings, which are provided for the purposes of illustration and not by way of limitation, the invention is embodied in a multi-stranded micro-cable formed of a plurality of flexible twisted strands of a resilient material with the cable including at least one radiopaque strand. In a presently preferred embodiment of the invention illustrated in FIG. 1, the multi-stranded micro-cable 10 is approximately from 0.0021 to 0.0045 inches in diameter, and comprises a plurality of flexible twisted strands 12 of nickel-titanium alloy, with at least one centrally, axially disposed radiopaque wire 14 which is approximately from 0.0007 to 0.0015 inches in diameter. While the above stated diameters represent those presently known to be compatible with the invention, larger or smaller diameters may be useful for particular applications. The central radiopaque wire 14 can be formed of platinum or gold, for example, or other similar suitable radiopaque metals, in order to provide a radiopaque marker of the deployed configuration of a device made of the cable during vascular surgery.

There are numerous benefits to the novel construction of the invention for use in interventional devices and the like. By using the stranded or micro-cable construction of the invention, a device made from the micro-cable becomes virtually kink resistant compared to the single strand wires now commonly used in micro-coils. The multi-strand cable construction of the invention allows the micro-wires of the cable to slip across each other and reinforce each other rather than break or take a set. Also, by incorporating a stranded radiopaque material such as platinum, tungsten or gold into the cable construction, the device is radiopaque in sizes much smaller than with other constructions. The micro-cable construction of the invention can be used to produce soft, kink resistant, radiopaque stents, guidewires, guidewire distal tips, and micro-coils.

Figures 1, 2:
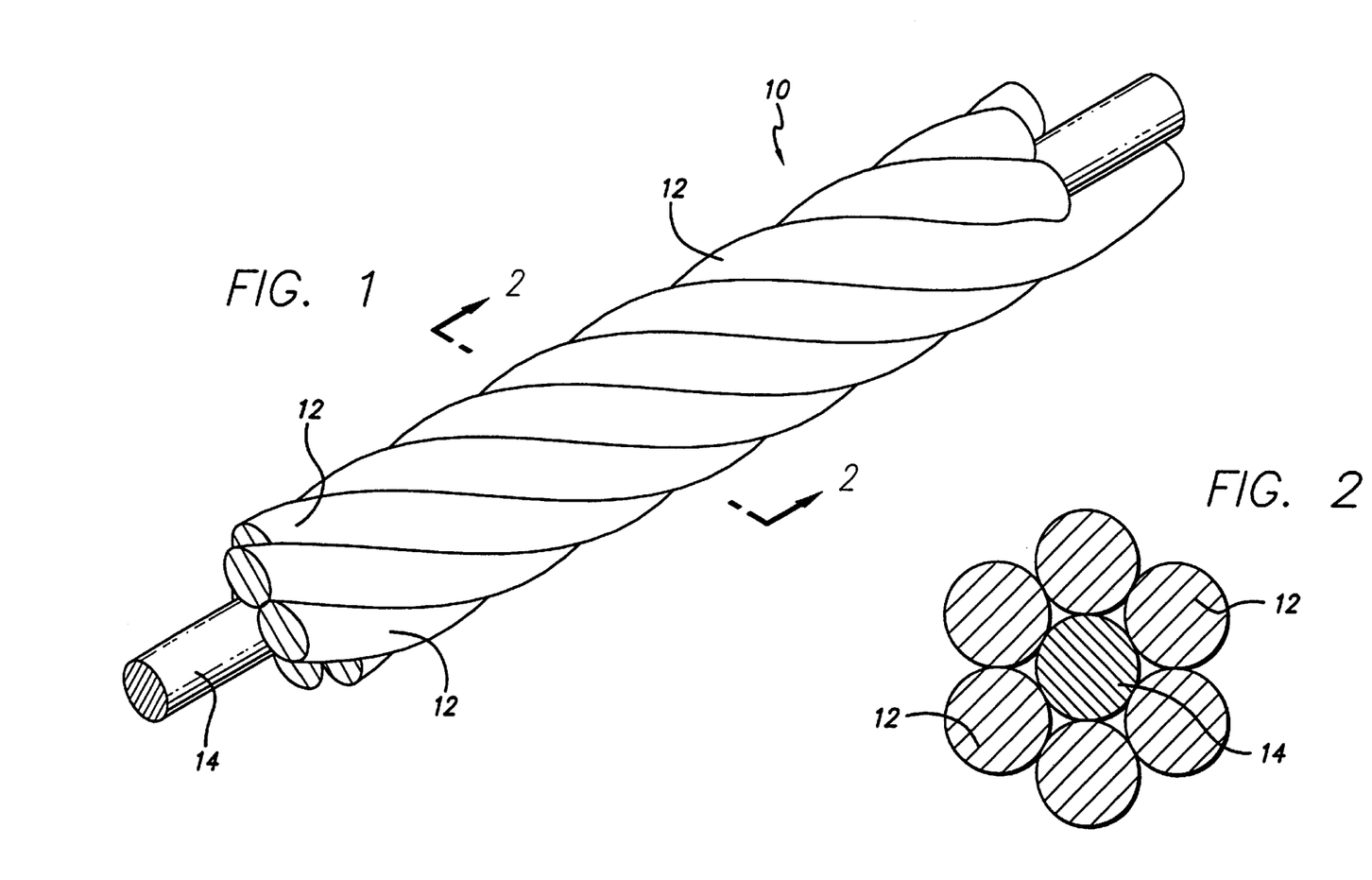
FIG. 1 is a perspective of a radiopaque microstrand cable constructed according to the invention.
FIG. 2 is a cross-section at 2—2 of FIG. 1.

FIG. 2 is a cross-section of the micro-cable of FIG. 1 at 2—2 illustrating one presently preferred arrangement of the strands within the cable. In this embodiment, the exterior strands 12 are formed of a resilient material chosen to provide the characteristics desired for a specific application in interventional therapies. In a presently preferred embodiment, this material is a nickel titanium super-elastic alloy which is heat treated such that the alloy is highly flexible at a temperature appropriate for introduction into the body via a catheter. By choosing such a material for micro-coils and the like, the devices formed from the micro-cable can be relatively easily placed into the appropriate body cavity and after placement, the device will take on a shape designed to optimize the therapeutic purposes desired for the device. As illustrated in FIG. 2, such a cable can have a central core 14 of a radiopaque material such as gold or platinum, thus dramatically enhancing the radiopacity of the cable. Even a solid super-elastic wire of the same diameter as the cable would have substantially less radiopacity than the cable of the invention with the central gold or platinum wire and the construction of the invention provides numerous other highly desirable characteristics. Among these characteristics is the relative flexibility and resistance to kinking of the cable compared to an equivalent single wire and substantially greater accommodation of the cable to bending, etc., with resultant lessening of trauma to the surrounding tissue and ease of placement in a small body cavity.

Figure 3:
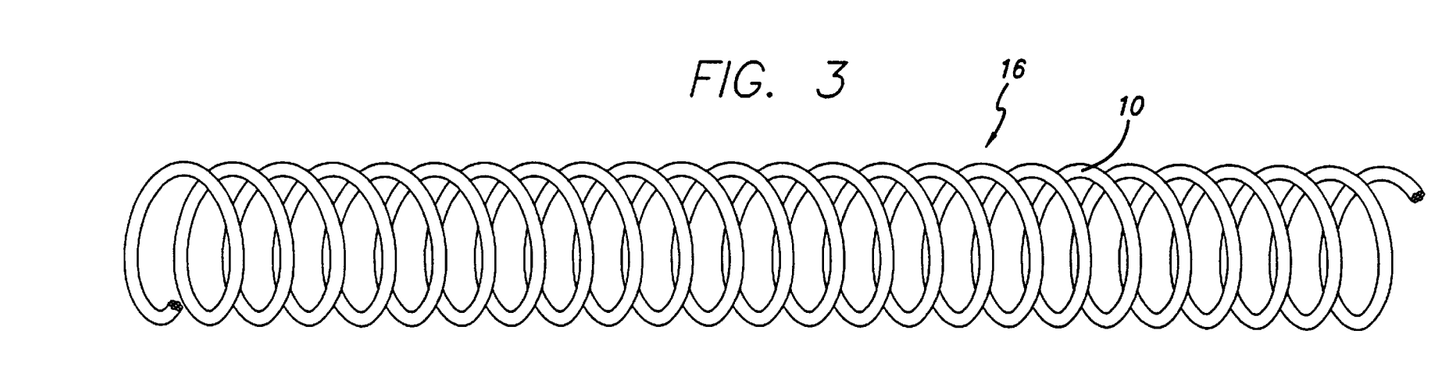
FIG. 3 is a helical vasooclusive coil formed of the cable of the invention.
Figure 4:
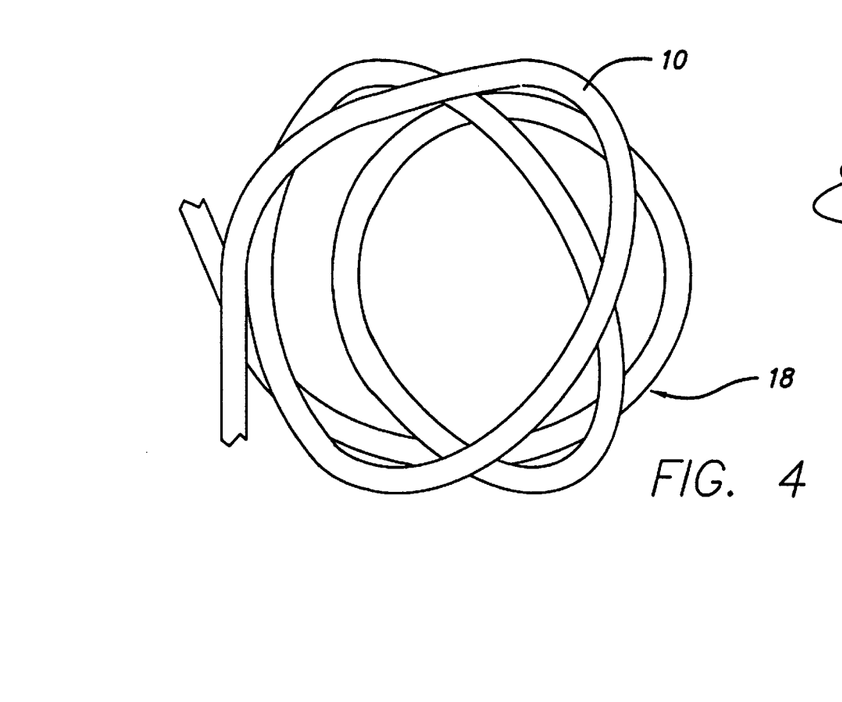
FIG. 4 is a spherical vasooclusive structure formed using the cable of the invention.
Figure 5:
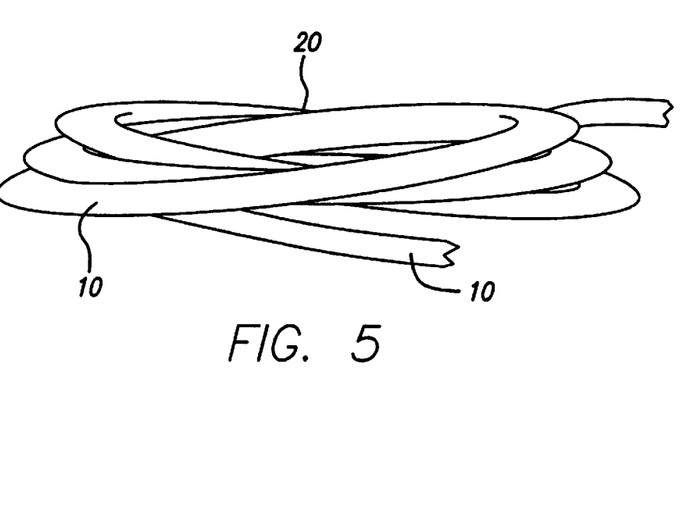
FIG. 5 is a stacked coil vasooclusive device formed using the cable of the invention.

One advantageous application of the invention is to vasooclusive devices formed of the micro-cable for insertion into aneurysms and other vascular defects for the purpose of occluding flow to the aneurysm. FIG. 3 illustrates a helically wound coil 16 of micro-cable 10 which is formed to fit within a micro-catheter for insertion into an area upon which a therapeutic procedure is to be performed. While a helical coil is illustrated, it will be appreciated that numerous other secondary shapes can be formed from the cable of the invention. More specifically, as illustrated in FIG. 4, a three dimensional, essentially spherical, device 18 can be formed of the cable 10, (or even of a coil of the cable, if appropriate) at a temperature sufficient to heat treat the material and thereby create a memory of the desired shape. The device is then inserted into a catheter from which it may be deployed into an aneurysm or the like. The teachings of U.S. Pat. No. 5,645,558 describe the construction of such a device out of flexible wire and are incorporated by referenced herein. FIG. 5 illustrates a collapsed coil configuration 20 for a vasooclusive device which also can be formed from the cable of the invention and is used for the purposes of insertion into aneurysms and other defects that have relatively large entry necks compared to their internal volume.

Figure 6:
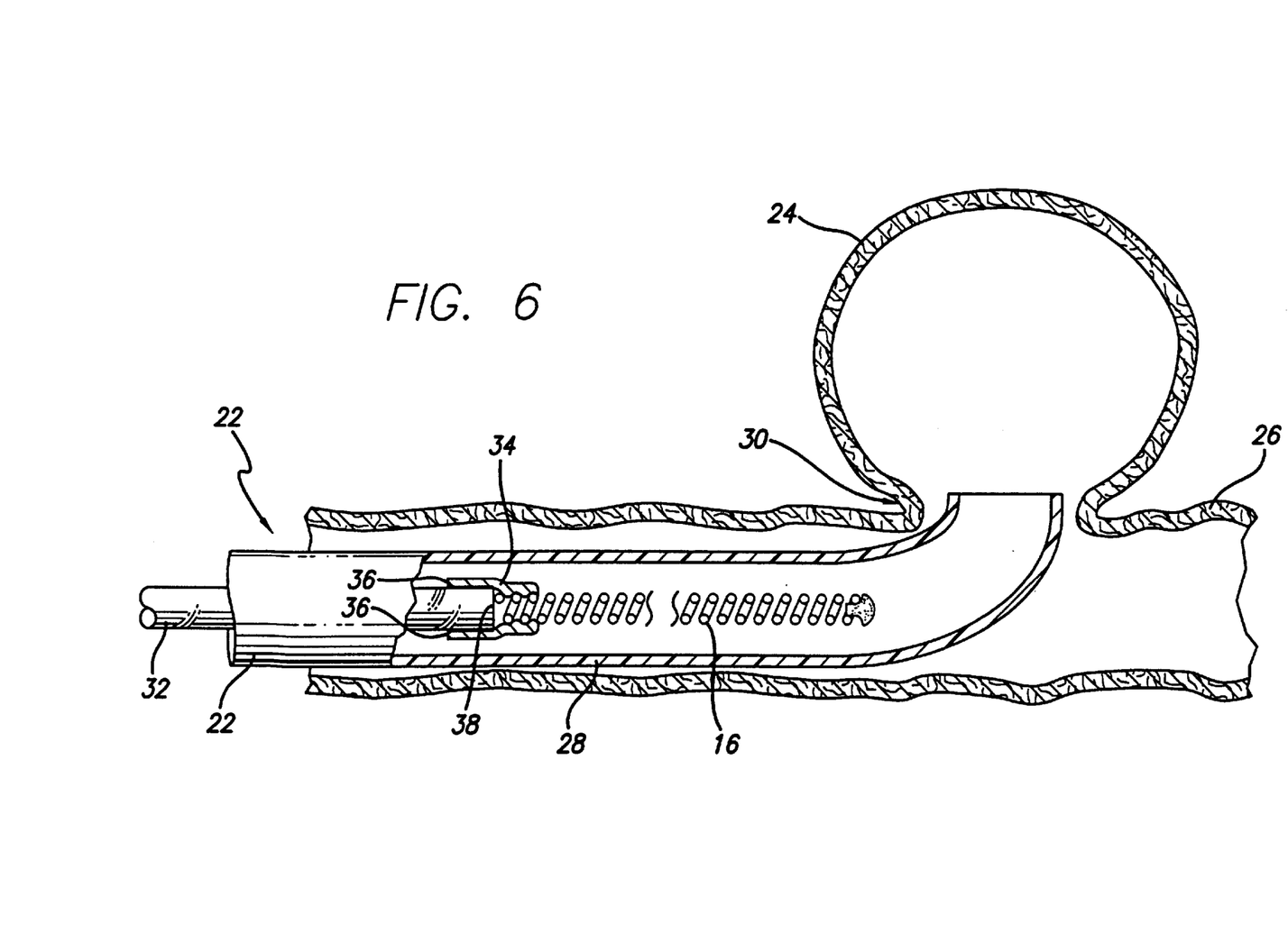
FIG. 6 is a cross section of a vascular member with an aneurysm illustrating the approach of a vasooclusive coil towards the aneurysm.
Figure 7:
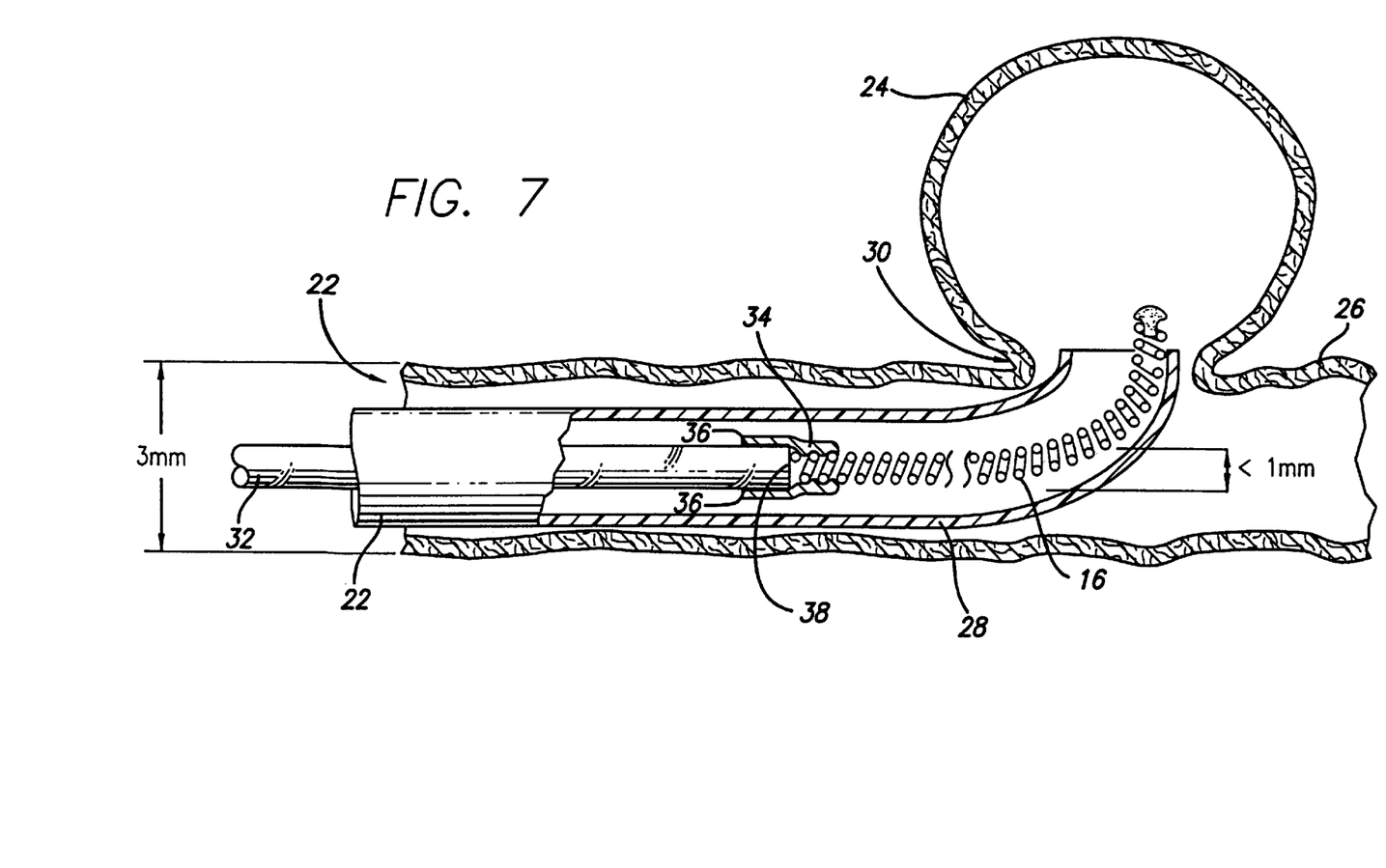
FIG. 7 is an illustration of a vasooclusive coil which has been introduced into an aneurysm preparatory to being deployed within the aneurysm.

FIG. 6 is an illustration of a catheter 22 using a coil 16 as a vasooclusive device made of the present invention and used for insertion into an aneurysm 24 projecting laterally from a blood vessel 26. The coil 16 is contained within the outer housing 28 of a micro-catheter that is used to house the coil prior to deployment. The end of the catheter housing 28 is introduced into the opening 30 of the aneurism 24 by use of a guide wire (note shown). Thereafter, the vasooclusive coil 16, and a pusher 32 are introduced into the catheter to provide for insertion of the vasooclusive device into the aneurysm. In a presently preferred embodiment, the coil 16 formed of the cable of the invention is retained to an optical fiber pusher 32 which is attached to the coil by a collar of shape memory plastic material 34 as described in co-pending application Ser. Nos. 09/218,117 and 09/072,314 the disclosure of which are incorporated herein by reference. As shown in FIG. 7, the coil is introduced into the aneurysm and is then pushed from the micro-catheter until it fills the cavity.

Those skilled in the art will recognize that it is sometimes the case that the vasooclusive device must be withdrawn after it is fully or partly inserted into the aneurysm. In such a case, there is a danger that the coil will be stretched beyond its elastic range or kink, or otherwise deform and make withdrawal difficult. Those skilled in the art will also recognize that it is sometimes advantageous to form vasooclusive devices of secondary shapes which are based upon a basic configuration of a coil or the like. The present invention includes such applications within the scope of the invention. However, when vasooclusive devices made of even super-elastic material are used, it is sometimes the case that the devices will be stretched or kinked when withdrawal is attempted. The cable of the present invention substantially reduces the probability that kinking or stretching beyond yield will occur in a given instance, while at the same time providing radiopacity not available with other constructions. Thus, the present invention represents an important forward step in the technology of interventional therapy.

In one presently preferred embodiment, the shape memory collar 34 is heated to a temperature which allows it to be shrunk onto coil 16. The collar is attached to optical fiber pusher 32 by an adhesive 36 which retains high strength at temperatures beyond the shape memory material transition point. After insertion, and when the operator is satisfied that the device is properly deployed, light energy from a source of coherent light is introduced into the proximal end of the optimal fiber (not shown) and propagated in the distal end 38 of the fiber to cause the shape memory material collar 34 to return to its previous shape and release coil 16. Those skilled in the art will recognize that the invention can also be used with a variety of other placement catheter systems, and it is not intended that the invention be limited to the placement concepts illustrated by way of example.

Figures 8, 9, 10:
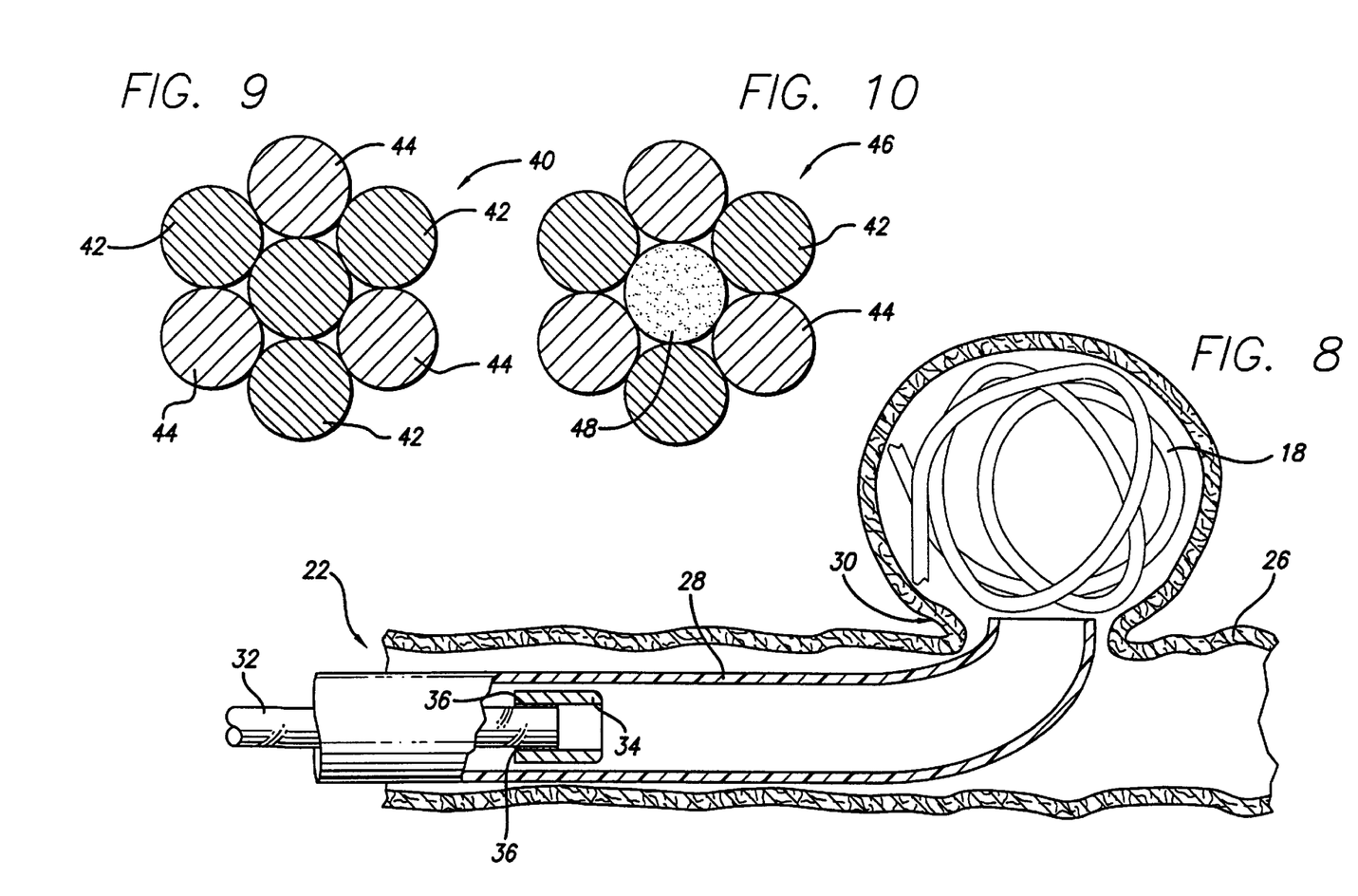
FIG. 8 is an illustration of a spherical vasooclusive coil formed with cable of the invention deployed within an aneurysm.
FIG. 9 is an alternate in a preferred embodiment of the invention including a plurality of radiopaque strands within the cable.
FIG. 10 is an alternate preferred embodiment incorporating a therapeutic member within the radiopaque cable of the invention.

Those skilled in the art will recognize that a number of shaped devices may be introduced into an area to be treated depending upon its geometry and the number of devices to be inserted. FIG. 8 illustrates an essentially spherical device 18 which has been deployed into such an aneurysm but it will commonly be found that a device such as that shown would then be supplemented by a further coiled device inserted within the space inside the spherical device to completely occlude flow from the artery to the aneurysm.

While one presently preferred implementation of the micro-cable of the invention has been illustrated, those skilled in the art will appreciate that other variations of the invention may have advantages for certain purposes. FIG. 9 is an example of one such construction 40 in which radiopacity is more desirable than in other forms and for that reason a number of radiopaque strands 42, in this illustration four in number, are formed into the cable along with three resilient material strands 44. It will also be appreciated that a larger or smaller number of strands may be incorporated into a given cable and the cables may be formed of multiple cables in order to provide desired bending and strength characteristics. It will also be appreciated by those skilled in the art that the invention is adaptable to the use of a variety of materials which by themselves would not have been easily adaptable to micro devices for interventional therapies. For instance, materials such as copper are useful for interuterine devices and the like, but copper wire, even when heavily alloyed, has certain limitations for use in such devices. By use of the present invention, composite cables incorporating one or more strands of a desired material can be configured with other strands providing strength, flexibility, shape memory, super-elasticity, radiopacity or the like for previously unavailable characteristics in micro devices.

The invention is also adaptable to numerous other purposes. FIG. 10 illustrates a cross-section of a further preferred embodiment in which radiopaque strands 42 and resilient strands 44 form a portion of the cable 46 and a therapeutic agent 48 is contained in one of the strands. Such a therapeutic agent can include human growth hormone, hydrogels, or a variety of other agents which will serve to provide desired therapeutic capabilities when placed within a specific area of the body being treated by use of the micro-catheter. Depending upon the application of the therapeutic agent, its method of action and the delay, if any, in the time after placement in which the therapeutic action is desired, the agent strand may be placed in any of a variety of positions with the cable, from core wire outward. Also, it may be desirable to coat one or more strands with a therapeutic material for certain purposes. At least one of the strands in the core or exterior strands can comprise a therapeutic agent, such as a copper or copper alloy wire or any of a variety of therapeutically active metals, alloys or components, a fiber such as Dacron (polyester), polyglycolic acid, polylactic acid, fluoropolymers, nylon, polyaramid fiber (e.g.Kevlar®), or silk chosen for thrombogenicity. Since the micro-cable consists of stranded parts, one or more strands may be longer than others, or even intermittently terminated, to thereby extend beyond the diameter of the remaining strands and thereby increase the therapeutic effect of that strand. Alternatively, at least one of the strands can be coated with or impregnated with a therapeutic material, which can include, but is not limited to, any one or combination of human growth hormone, genetic material, antigens, hydrogels, collagen, bio-absorbable polymers such as lactic acids/glycolic acids, caprolactam or microcellular foam. In addition, the therapeutic element can comprise a means to conduct energy, such as an optical fiber to conduct light energy, or a means to conduct electrical energy, such as a means to conduct radio frequency energy. Such constructions are contemplated within the scope of the invention.

Figures 11, 12:
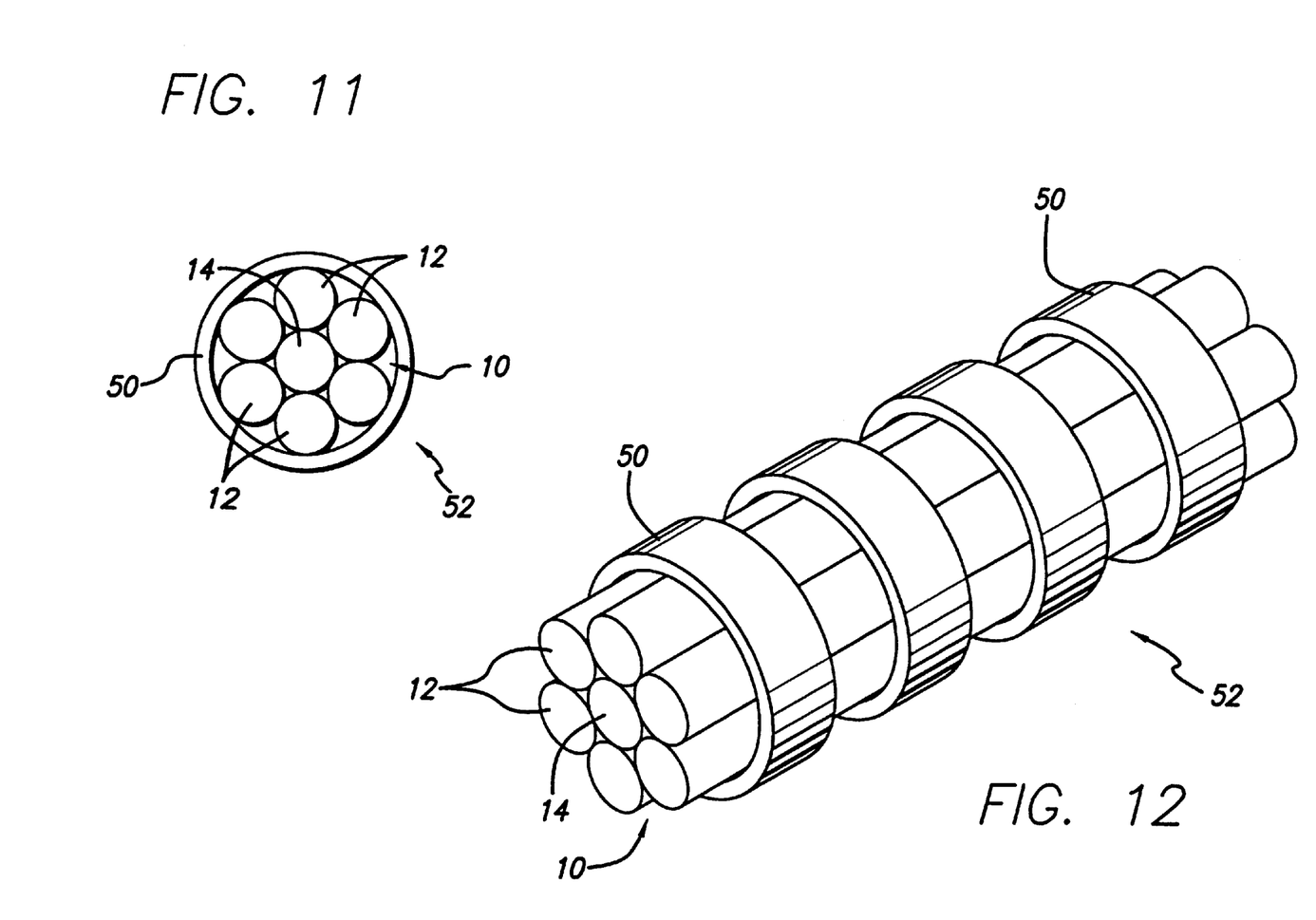
FIG. 11 is an alternate preferred embodiment of the present invention wherein strands of the cable are arranged within an exterior binding consisting of multiple straps about the cable.
FIG. 12 is a perspective view of the embodiment of FIG. 11.

FIG. 11 illustrates a cross-section of an additional presently preferred embodiment of the invention in which the strands 12, 14 of the micro-cable 10 are bundled and banded at intervals by bands 50 to produce a composite banded cable 52 in order to provide increased flexibility without unraveling or dislocation of the strands in the cable. FIG. 12 is a perspective view of the banded cable 50 of this embodiment. While the illustrated configuration shows the strands being laid parallel within the cable, it is also possible in this construction to include both twisted cables as the primary cables 10 within the outer bands 50 to form the composite cable 52. This configuration can use one or more longitudinal strands 14 which are radiopaque, thus providing a continuous indication of radiopacity within the cable. The composite cable can further comprise at least one longitudinal sensing element for sensing a parameter, such as an optical imaging element, i.e., where the sensing element can comprises an optical fiber. Alternatively, the sensing element can comprise a thermal imaging element, or an ultrasound imaging element, for example. As a further alternative embodiment, it is possible for the longitudinal cable 52 to be formed of a single inner cable 10 with bands 50.

Figures 13, 14A, 14B:
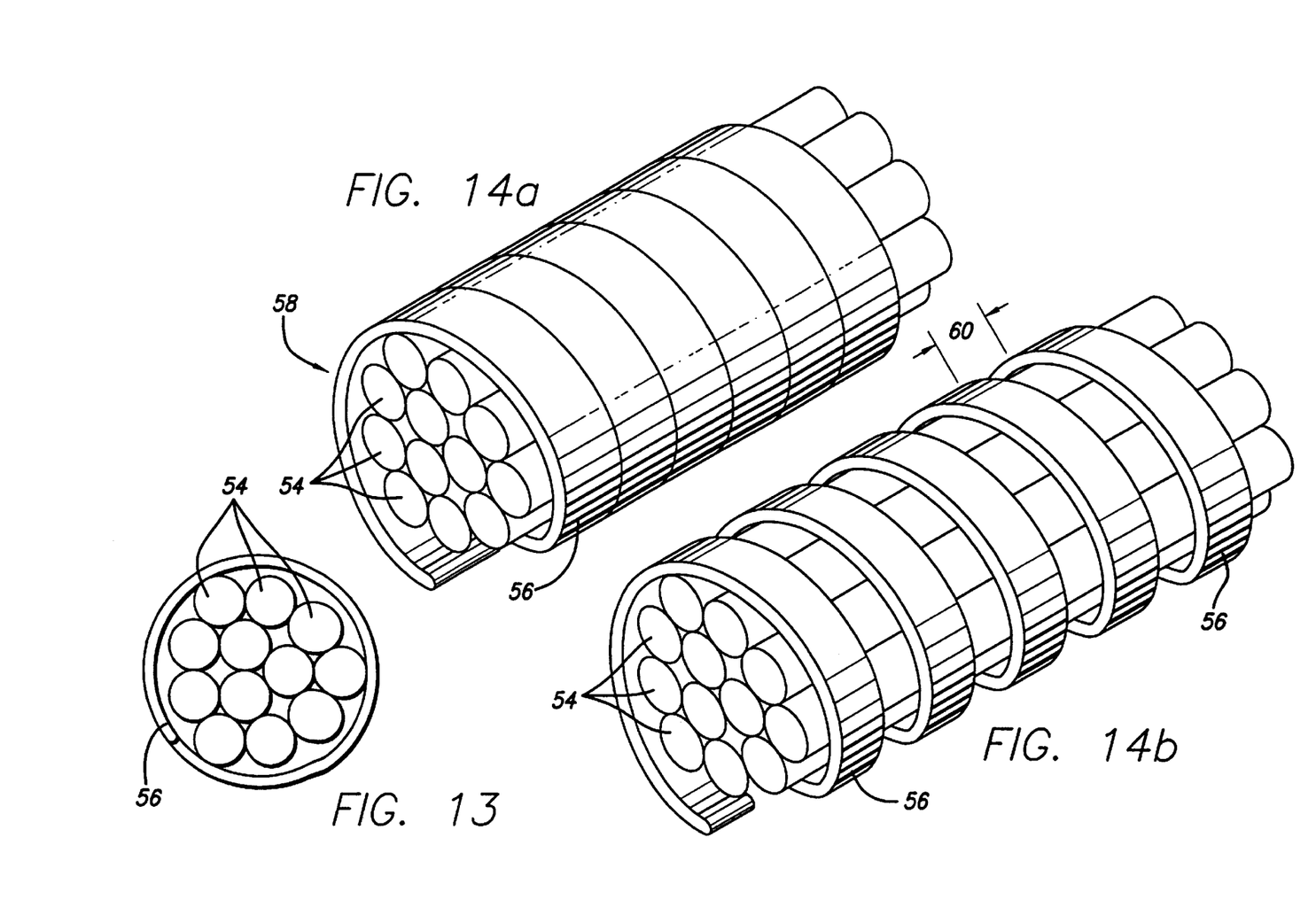
FIG. 13 is an alternative embodiment to the embodiment of FIG. 12 wherein the external binding of the cable represents a sheath wound about the cable.
FIGS. 14a and 14b are perspectives of alternative embodiments of the embodiment of FIG. 13.

FIG. 13 illustrates a further embodiment of the invention in which longitudinal strands of cables 54 are contained within a wound cover 56 for the purposes of providing a composite guide wire or the like 58 having improved torqueability. The strands of the micro-cable can also be bundled by at least one outer cover or sheath to constrain the strands of the micro-cable about a longitudinal axis to produce a composite banded cable. The outer sheath can comprise a containment strand wound about the strands and made of a low friction material, such as a fluoropolymer, for example, or a heat shrinkable plastic tube. In one feature of the fifth aspect of the invention, a plurality of heat shrink plastic covers are placed over the strands of the micro-cable to provide bending stiffness in the cable. Such a construction has particular advantages for guidewire designs having improved radiopacity in very small diameters. It will be appreciated that in this configuration, as well as the other longitudinally arranged multi-stranded cables, the number of strands and the degree to which they extend along the cable within the sheath is a variable which can be used to provide increased stiffness, pushability and torqueability in some sections with greater flexibility in others. Additionally, composite cables according to the invention can incorporate additional elements normally not available in solid guide wires, such as optical, thermal or ultrasound imaging elements, therapeutic agent delivery catheters, and can take advantage of materials which are not readily adaptable to prior art catheter or guide wire designs incorporating a primary wire structured element. FIGS. 14a and 14b illustrate a further variable available because of the invention; the exterior wrapped cover 56 can be wound at greater or lesser intervals 60 along the outside to provide variations in the torqueability and stiffness of the composite cable. Also, the thickness and width of the wrapping cover 56, as well as its material composition along the composite guide wire 58, can offer further capabilities for customizing the design for various applications. These advantages can be combined with the benefits of shape memory or super-elastic alloys to create guidewires and other devices with heretofore unavailable capabilities.

Figures 15, 16:
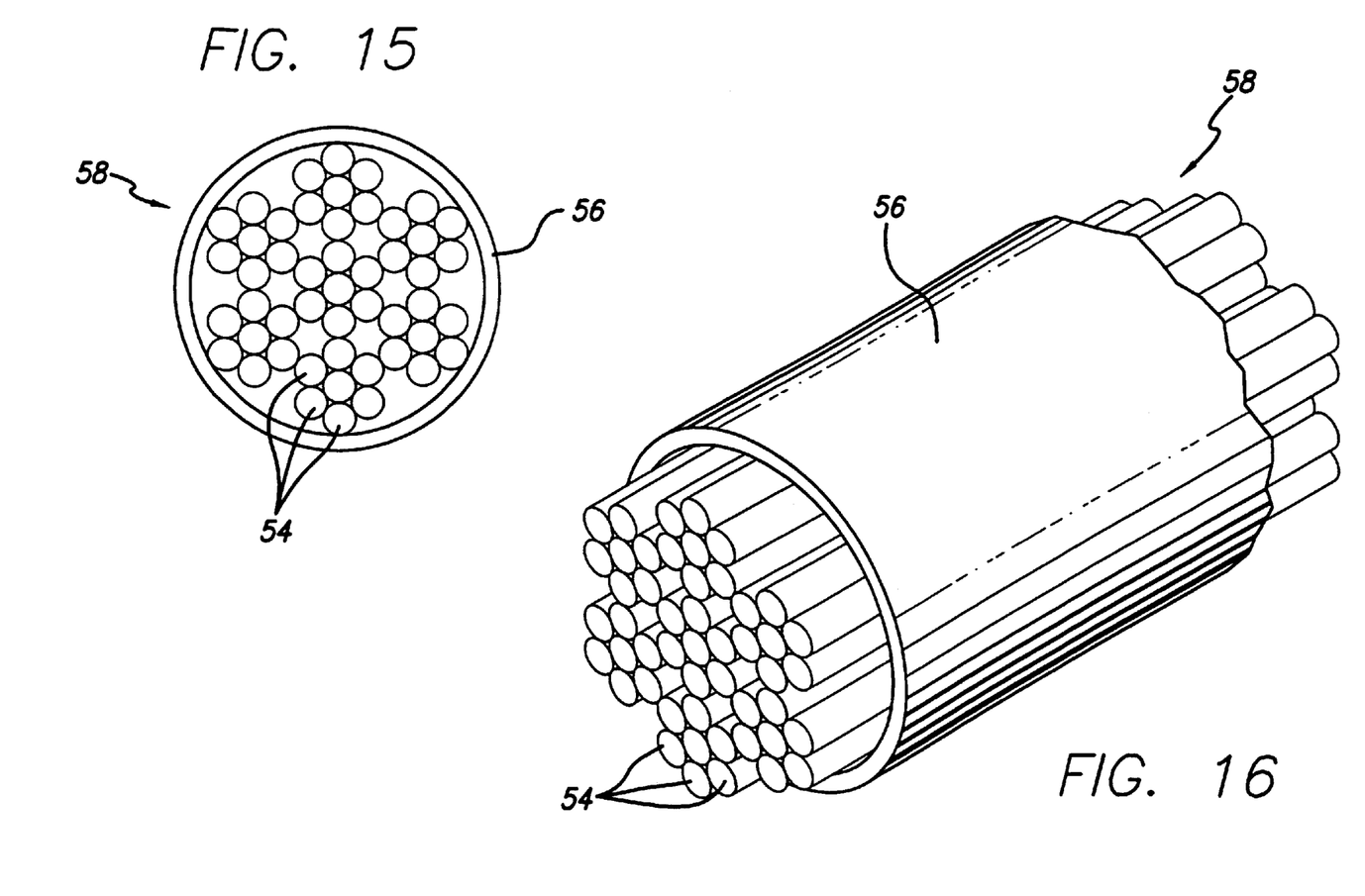
FIG. 15 is a cross-section of an alternative embodiment in which a plurality of multi-strand cables are included within an external sheath surrounding the cable.
FIG. 16 is a perspective view of the embodiment of FIG. 14.

FIG. 15 illustrates a cross-section of a micro-cable according to the invention which has at least one overall exterior sheath to contain the micro-cable. The micro-cable may be made of one or more multiple strand elements which may further include twisted or longitudinal strands within their construction. The sheath may also be used to control the torqueability characteristics of the cable and as discussed in co-pending application Ser. No. 09/275,485, the sheath may be multi-layered with different materials in order to provide a graduated bending and stiffness characteristic over the length of the cable.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A multi-stranded micro-cable for use in interventional therapy and vascular surgery comprising:

a plurality of flexible twisted strands of a resilient material longitudinally arranged in said cable, at least one of said flexible twisted strands being of radiopaque material, and wherein at least one of said strands comprises a shape memory material; and a sheath formed of a containment strand wound about said plurality of flexible twisted strands to constrain said strands of said micro-cable about a longitudinal axis.

2. The multi-stranded micro-cable of claim 1 wherein said shape memory material comprises a nickel titanium alloy.

3. The multi-stranded micro-cable of claim 1 wherein said shape memory material further comprises a nickel-titanium alloy.

4. The multi-stranded micro-cable of claim 1 wherein said shape memory material further comprises a shape memory polymer.

5. The multi-stranded micro-cable of claim 1, wherein a plurality of flexible strands are twisted about a longitudinal axis, at least one of said twisted strands being of a radiopaque material.

6. A multi-stranded micro-cable for use in interventional therapy and vascular surgery comprising:

a plurality of flexible twisted strands of a resilient material longitudinally arranged in said cable, at least one of said flexible twisted strands being of radiopaque material, wherein at least one of said strands comprises a super-elastic material; and a sheath formed of a containment strand wound about said plurality of flexible twisted strands to constrain said strands of said micro-cable about a longitudinal axis.

7. The multi-stranded micro-cable of claim 6 wherein said super-elastic material comprises a nickel titanium alloy.

8. A multi-stranded micro-cable for use in interventional therapy and vascular surgery comprising:

a plurality of flexible twisted strands of a resilient material longitudinally arranged in said cable, at least one of said flexible twisted strands being of radiopaque material;

a sheath formed of a containment strand wound about said plurality of flexible twisted strands to constrain said strands of said micro-cable about a longitudinal axis; and an outer flexible sheath of low friction material.

9. The multi-stranded micro-cable of claim 8 wherein said outer sheath comprises a fluoropolymer.

10. A multi-stranded micro-cable for use in interventional therapy and vascular surgery comprising:

a plurality of flexible twisted strands of a resilient material longitudinally arranged in said cable, at least one of said flexible twisted strands being of radiopaque material, wherein said plurality of flexible twisted strands of a resilient material are comprised of a super-elastic material; and a sheath formed of a containment strand wound about said plurality of flexible twisted strands to constrain said strands of said micro-cable about a longitudinal axis.

11. A multi-stranded micro-cable for use in interventional therapy and vascular surgery comprising:

a plurality of flexible twisted strands of a resilient material longitudinally arranged in said cable, at least one of said flexible twisted strands being of radiopaque material, wherein said plurality of flexible strands of a resilient material are comprised of a shape memory material; and a sheath formed of a containment strand wound about said plurality of flexible twisted strands to constrain said strands of said micro-cable about a longitudinal axis.

12. A multi-stranded micro-cable for use in interventional therapy and vascular surgery comprising:

a plurality of flexible twisted strands of a resilient material longitudinally arranged in said cable, at least one of said flexible twisted strands being of radiopaque material, and wherein said radiopaque strand comprises a platinum strand; and a sheath formed of a containment strand wound about said plurality of flexible twisted strands to constrain said strands of said micro-cable about a longitudinal axis.

13. A multi-stranded micro-cable for use in interventional therapy and vascular surgery comprising:

a plurality of flexible twisted strands of a resilient material longitudinally arranged in said cable, at least one of said flexible twisted strands being of radiopaque material, and wherein said radiopaque strand comprises a gold strand; and a sheath formed of a containment strand wound about said plurality of flexible twisted strands to constrain said strands of said micro-cable about a longitudinal axis.

14. A multi-stranded micro-cable for use in interventional therapy and vascular surgery comprising:

a plurality of flexible twisted strands of a resilient material longitudinally arranged in said cable, at least one of said flexible twisted strands being of radiopaque material, and wherein said radiopaque strand comprises a tungsten strand; and a sheath formed of a containment strand wound about said plurality of flexible twisted strands to constrain said strands of said micro-cable about a longitudinal axis.

15. A multi-stranded micro-cable for use in interventional therapy and vascular surgery comprising:

a plurality of flexible twisted strands of a resilient material longitudinally arranged in said cable, a plurality of said flexible twisted strands being of radiopaque material; and a sheath formed of a containment strand wound about said plurality of flexible twisted strands to constrain said strands of said micro-cable about a longitudinal axis.

16. A multi-stranded micro-cable for use in interventional therapy and vascular surgery comprising:

a plurality of flexible twisted strands of a resilient material longitudinally arranged in said cable, at least one of said flexible twisted strands being of radiopaque material;

at least one strand of a therapeutic material; and a sheath formed of a containment strand wound about said plurality of flexible twisted strands to constrain said strands of said micro-cable about a longitudinal axis.

17. The multi-stranded micro-cable of claim 16 wherein said strand of therapeutic material comprises hydrogel.

18. The multi-stranded micro-cable of claim 16 wherein said strand of therapeutic material comprises human growth hormone.

19. A composite wire for use in interventional therapy or vascular surgery, comprising:

a plurality of longitudinal structural strands, each of said strands being made of a resilient shape memory material;

at least one longitudinal radiopaque strand extending over a portion of the composite wire;

at least one longitudinal sensing element for sensing a parameter, wherein said sensing element comprises an optical fiber; and an outer sheath of material to provide bending stiffness and constrain said longitudinal strands about said longitudinal axis.

20. A composite wire for use in interventional therapy or vascular surgery, comprising;

a plurality of longitudinal structural strands, each of said strands being made of a resilient shape memory material;

at least one longitudinal radiopaque strand extending over a portion of the composite wire;

at least one longitudinal therapeutic element comprising means to conduct energy for providing a therapeutic effect at a location near the distal end of said wire, wherein said means to conduct energy comprises an optical fiber; and an outer sheath of material to provide bending stiffness and constrain said longitudinal strands about said longitudinal axis.

* * * * *

UNITED STATES PATENT AND TRADEMARK OFFICE
CERTIFICATE OF CORRECTION

PATENT NO. : 6,168,570 B1
DATED : Jan. 2, 2001
INVENTOR(S) : David A. Ferrera

It is certified that error appears in the above-identified patent and that said Letters Patent is hereby corrected as shown below:

Title page, under U.S. PATENT DOCUMENTS, page 2, second column, 36th entry, change "5,406,377" to read --5,405,377--.

Title page, under FOREIGN PATENT DOCUMENTS, page 3, first column, 16th entry, change "WO 94/18585" to read --WO 95/18585--.

Signed and Sealed this

Twenty-ninth Day of May, 2001

Attest:

NICHOLAS P. GODICI

Attesting Officer

Acting Director of the United States Patent and Trademark Office